United States Patent [19]

Tritsch

[11] 4,389,212
[45] Jun. 21, 1983

[54] DIAPER WITH POTENTIALLY ELASTIC TAPE FASTENER

[75] Inventor: Ludwig Tritsch, Wilmette, Ill.

[73] Assignee: Personal Products Company, Milltown, N.J.

[21] Appl. No.: 326,726

[22] Filed: Dec. 2, 1981

[51] Int. Cl.³ .................................................. A41B 13/02
[52] U.S. Cl. .................................................. 604/389
[58] Field of Search .................. 604/385, 389–390; 24/304

[56] References Cited

U.S. PATENT DOCUMENTS

| | | | |
|---|---|---|---|
| 3,848,594 | 11/1974 | Buell | 604/390 |
| 3,869,761 | 3/1975 | Schaar | 604/390 |
| 3,920,018 | 11/1975 | Schaar | 604/389 |
| 3,955,576 | 5/1976 | Safford | 604/389 |

*Primary Examiner*—C. Fred Rosenbaum
*Attorney, Agent, or Firm*—Martha A. Michaels

[57] ABSTRACT

A disposable diaper having a facing sheet defining a diaper inside surface for direction toward the wearer and a backing sheet defining a diaper outside surface is provided with adhesive tape tabs comprising first and second anchoring portions and an attachment portion. The anchoring portions are attached to the inside surface and the outside surface of the diaper at a marginal portion thereof. One of the anchoring portions is made from elastic web material, and the other anchoring portion is made from inelastic web material. The attachment portion is temporarily attached to the inelastic anchoring portion and adhesively secured to the elastic anchoring portion. In use, the temporary attachment is detached leaving only the adhesive securement of the attachment portion to the elastic anchoring portion to provide an elastic tape tab fastener.

6 Claims, 8 Drawing Figures

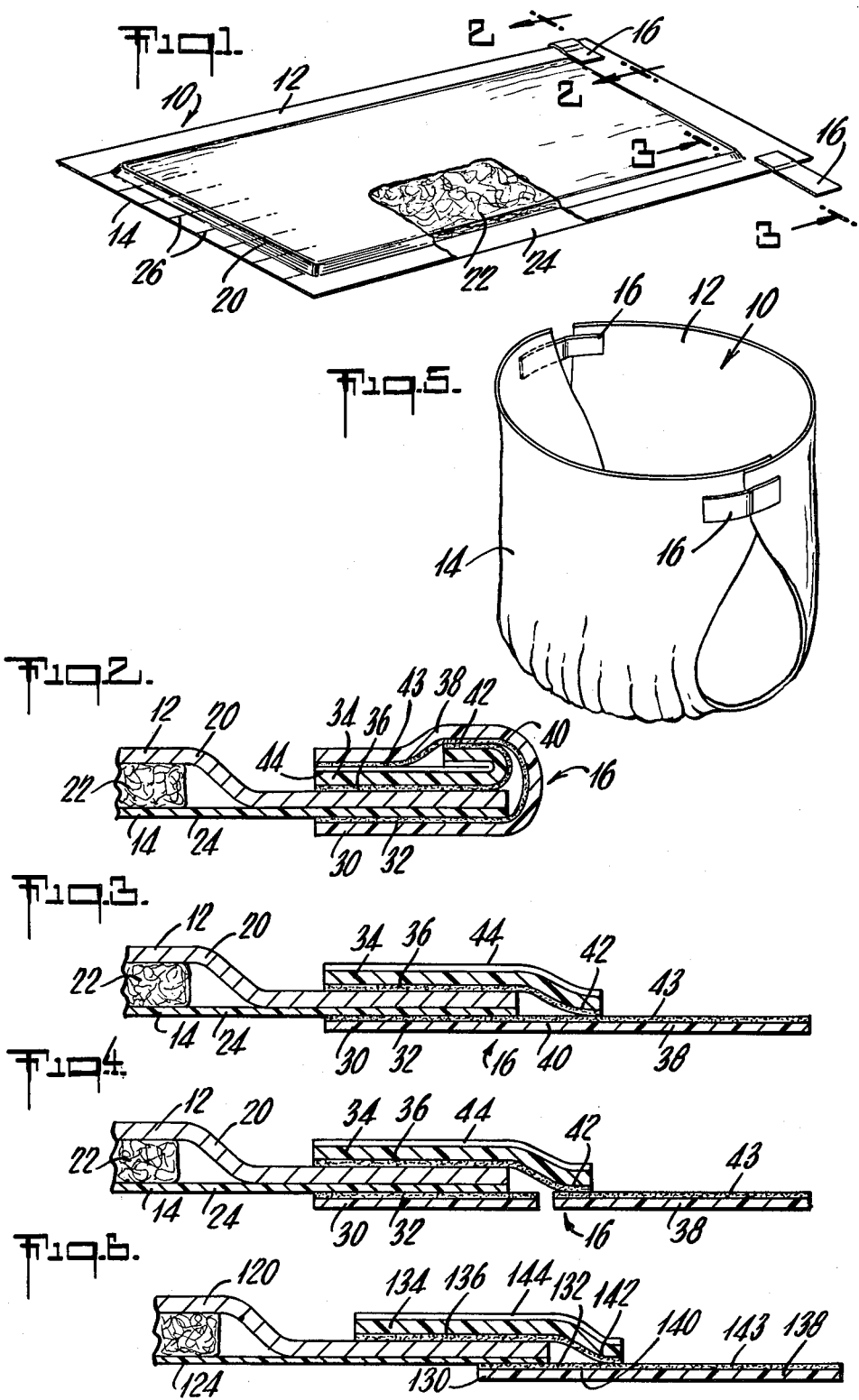

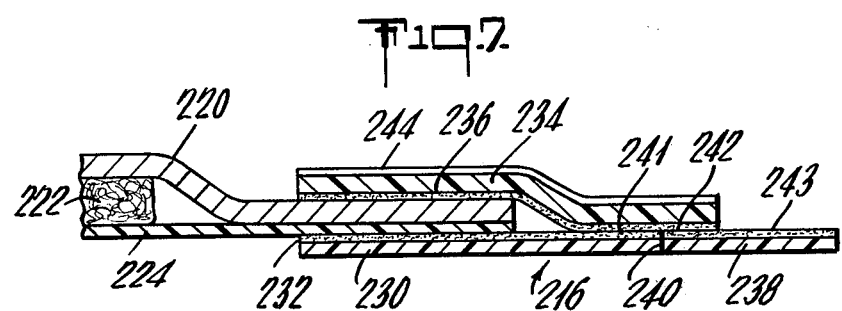
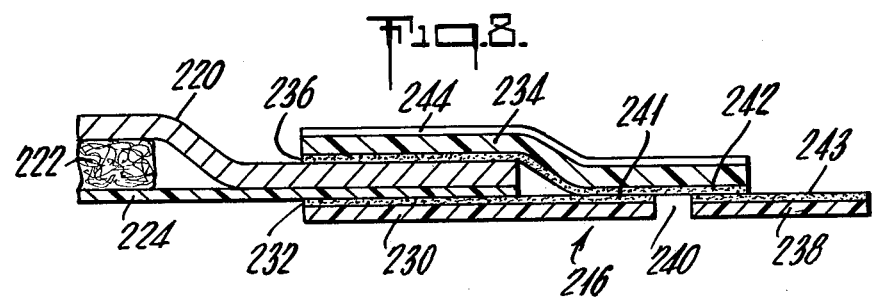

DIAPER WITH POTENTIALLY ELASTIC TAPE FASTENER

BACKGROUND OF THE INVENTION

This invention relates to disposable diapers. More particularly, this invention relates to disposable diapers adapted to be secured in place by adhesive tape tabs.

Disposable diapers provide substantial advantages and convenience over diapers intended to be laundered and reused, particularly when they are used away from the home. In recent years, many different disposable diapers have been proposed and some have been successful in the marketplace. Typical disposable diaper structures comprise a moisture-retaining layer of high liquid holding capacity placed between a moisture-impervious backing sheet generally made of a plastic film such as polyethylene film and the like and a moisture-pervious facing sheet. Typical disposable diaper structures are shown in U.S. Pat. No. 3,612,055 to Mesek et al, U.S. Pat. No. Re. 26,151 to Duncan et al, and U.S. Pat. No. 3,860,003 to Buell.

As may be seen from the above-cited patents, it is desirable to obviate the problems that are inherent in closure systems which utilize extraneous fasteners such as safety pins, snaps, and zippers. To this end, various adhesive closure systems have presented acceptable solutions. Examples of suitable adhesive closure systems are disclosed in U.S. Pat. No. 3,616,114 to Hamaguchi et al and U.S. Pat. No. 3,833,456 to Reed et al. There are many other similar types of adhesive tape tab closure systems disclosed in a myriad of other patents.

In order to try to improve the fit of the diaper, a number of ways have been attempted to provide elastic waistband means in the diaper. One such attempt is disclosed in U.S. Pat. No. 3,800,796 to Jacob, issued Apr. 2, 1974, which provides an elastic tape tab means. In U.S. Pat. No. 3,800,796, an elastic section is placed in the backing web for application of the pressure-sensitive adhesive tape tab means of the diaper. It is believed this concept has never been developed commercially because of the inherent problems in handling such elastic web materials at high speed manufacturing operations. Disposable diapers must be made at high rates of speed in order to be manufactured economically. Trying to place unstable elastic web material accurately at the marginal edges of the diaper at high rates of speed is extremely difficult and greatly reduces manufacturing efficiencies. Other techniques for providing elastic characteristics in tape tabs are disclosed in U.S. Pat. Nos. 4,158,363; 4,090,516; 4,074,716; and 4,066,681, all to Schaar.

SUMMARY OF THE INVENTION

The present invention provides a new adhesive tape tab fastener for a diaper having elastic characteristics. The new fastener is a stable structure in its configuration when it is applied to the marginal edge of the diaper. Once applied to the diaper, the new fastener is automatically activated to render it elastic when the diaper is placed on the wearer.

In accordance with the present invention, tape tabs are used on each side of a diaper to secure the diaper about the wearer. Each tape tab includes a first anchoring portion secured to the diaper outside surface at a marginal portion of the diaper. Each tape tab also includes a second anchoring portion secured to the diaper inside surface at a marginal portion of the diaper. In a preferred embodiment of my new tape tab, one of the anchoring portions is made from elastic web material and the other anchoring portion is made from inelastic web material. Each tape tab has an attachment portion temporarily attached to the inelastic anchoring portion and adhesively secured to the elastic anchoring portion. The temporary attachment is such that it is broken and the attachment portion detached from the inelastic anchoring portion with a low amount of force leaving the attachment portion only adhesively secured to the elastic anchoring portion.

Each tape tab has its attachment portion having a free working end provided with a layer of pressure-sensitive adhesive on one face thereof. In a preferred embodiment of my new improved tape tab, the tape tab has release means on the outside surface of the second anchoring portion so that the free end is adhered to said release means for storage and then when removed from the release means is available for use in securing the diaper about the wearer.

The tape tab fasteners of the present invention are stable in their configuration when they are applied to the diaper in that the anchoring portion which is made of inelastic material and the attachment portion which is also made of inelastic material stabilize the entire structure. When the diaper is placed on the wearer, the mother takes the free working end of the attachment portion of the tape tab and pulls that about the waist of the baby to adhere it to the front waistband portion of the diaper. The temporary attachment between the attachment portion and the inelastic anchoring portion is such that the slight pull by the mother to provide a snug fit about the waist of the baby detaches the attachment portion from the inelastic anchoring portion. This leaves the attachment portion adhesively secured only to the elastic anchoring portion, hence, rendering the tape tab fastener elastic and providing elastic waistband means in the disposable diaper.

BRIEF DESCRIPTION OF THE DRAWINGS

FIG. 1 is a perspective view partially broken away to show interior detail of an open unfolded diaper in accordance with one of the embodiments of the invention;

FIG. 2 is an enlarged fragmentary cross-sectional view of the diaper of FIG. 1 taken along line 2—2;

FIG. 3 is an enlarged fragmentary cross-sectional view of the diaper in FIG. 1 taken along line 3—3;

FIG. 4 is an enlarged fragmentary cross-sectional view of the tape tab of FIG. 3 after it has been activated to render it elastic;

FIG. 5 is a perspective view of the diaper of FIG. 1 in a configuration assumed by the diaper when placed about a wearer;

FIG. 6 is an enlarged fragmentary cross-sectional view similar to FIG. 2 illustrating an alternative embodiment of the present invention;

FIG. 7 is an enlarged fragmentary cross-sectional view similar to FIG. 2 illustrating another embodiment of the present invention; and FIG. 8 is an enlarged fragmentary cross-sectional view of the tape tab of FIG. 7 after it has been activated to render it elastic.

DESCRIPTION OF THE PREFERRED EMBODIMENTS

In the following description, two-digit numerals are used to refer to the embodiment illustrated in FIGS.

1–5, three-digit numerals in the one-hundred series are used to refer to the embodiment illustrated in FIG. 6, and three-digit numerals in the two-hundred series are used to refer to the embodiment illustrated in FIGS. 7 and 8. The same last two digits in each numeral designates similar elements in the various embodiments.

The disposable diaper 10 illustrated in FIGS. 1 and 5 is a substantially quadrilateral configuration and presents an inside surface 12 for direction toward a wearer and an outside surface 14 for direction away from the wearer. Adhesive tape tab fastener means such as tab 16 are attached to the diaper 10 for securing the diaper about the wearer. As described in greater detail below, the tab 16 is movable from a folded over storage position, illustrated in FIG. 2, to a starting working position which is illustrated in FIG. 3 and the completed working position illustrated in FIG. 4.

Referring to FIGS. 1–4, the diaper 10 comprises a moisture-pervious facing sheet 20 defining a diaper inside surface 12 and an overlying moisture retaining absorbent pad 22 and a backing sheet 24 which is made of a moisture-impervious material and defines a diaper outside surface 14. The absorbent pad 22 is somewhat smaller than the backing sheet 24 and is centrally disposed thereon; however, the absorbent pad 22 can be made co-extensive with the backing sheet 24, if desired. The facing sheet 20 is substantially co-extensive with the backing sheet 24. Both the facing sheet 20 and the pad 22 can be anchored to the backing sheet 24 by means of adhesive beads 26, glue spots or any other convenient means. For example, if the backing sheet 24 is made of the thermoplastic material, the facing sheet 20 and the pad 22 can be attached thereto by heat bonding.

As illustrated in FIGS. 2, 3 and 4, an adhesive tab 16 comprises a first anchoring web 30, located at the marginal edge of the diaper and attached to the diaper outside surface by means of the pressure-sensitive adhesive 32. A second anchoring web 34 made from elastic material is attached to the diaper inside surface also by pressure-sensitive adhesive 36. The first and second anchoring webs are adhesively secured together at the marginal edges of the diaper. An attachment portion 38 is temporarily attached 40 to the first anchoring web and is adhesively secured 42 to the second anchoring web 34. The free working end of the attachment portion contains pressure-sensitive adhesive 43 on its working surface. On the outer surface of the first anchoring web there is a release coating 44, so that as shown in FIG. 2, the attachment portion, which has adhesive on its surface can be folded over and placed in a storage position against this release coating. In use, the attachment portion with the adhesive thereon is removed from the release coating into the position shown in FIG. 3.

The person putting the diaper on the wearer when applying the diaper tends to pull the tape tab tight. In doing so, the temporary attachment is broken, as seen in FIG. 4, and the attachment portion is no longer attached to the first anchoring web but is only adhesively secured to the second anchoring elastic web, thereby rendering the tape tab elastic in use. As may be clearly seen, the tape tab in its folded position and, as well, in its position in FIG. 3 and also when being applied to the diaper, in the manufacture of the diaper, is a stable member in that the elastic portion is always supported by inelastic material. However, when slight tugs are placed on the attachment portion of the tape tab in order to apply the diaper to the wearer, the temporary attachment is broken and the structure of the tape tab now is rendered elastic in use.

In the embodiment illustrated in FIG. 6, the inelastic anchoring portion 130 has been shortened considerably. This is feasible because in use the inelastic anchoring portion serves no functional purpose. Its functional purpose is in the manufacture of the diaper, but not in the use of the diaper. Hence, for economical reasons, it may be desirable to decrease considerably the amount of tape which is used on the tape tab. This may be readily accomplished by shortening the inelastic anchoring portion.

The remaining parts of the tape tab fastener depicted in FIG. 6 are the same as those depicted in FIGS. 2, 3, and 4. The inelastic anchoring portion 130 is attached to the diaper backing 124 by an adhesive layer 132. The elastic anchoring portion 134 is attached to the diaper facing 120 by adhesive 136. The attachment portion 138 which carries a pressure-sensitive adhesive 143 on its free working end is temporarily attached 140 to the inelastic anchoring portion 130 and adhesively secured 142 to the elastic anchoring portion. The elastic anchoring portion 134 carries a release coating 144 on its outer surface for placement of the attachment portion in the storage position.

In the embodiment illustrated in FIGS. 7 and 8, the first anchoring web 230 is adhesively secured 232 to the backing sheet 224 and to the second anchoring web 234. Securement to both the backing sheet and the first anchoring web 241 helps to distribute stress provided by applying the diaper to the wearer and subsequent wearing of the secured diaper. Referring to FIG. 8, it can be seen that the attachment portion 238 when applied, allows the elastic anchoring web 234 to extend beyond the point 240 at which it was temporarily attached without dislodging the attachment of the first and second anchoring webs to each other 241.

Release means such as region 44, 144 and 244 in FIGS. 2, 3, 4, 6, 7 and 8, may comprise a release coating such as a silicone release compound or the like on the outer face of the second anchoring portion. This coating is substantially co-extensive with the adhesive coating on the free working end of the attachment portion 38, 138 and 238 when the tab is folded in the storage position. If it is desirable to provide a gripping means to facilitate grasping the tab 16 to separate the adhesive coating on the free end from the release means, there are a number of ways this may be accomplished; for example, a short strip of material may be adhered to the outer edge of the free working end of the attachment portion, or the outer edge of the free working end of the attachment portion may be folded over on itself to provide a grasping means.

The inelastic anchoring portion and the attachment portion of the adhesive tabs suitable for the purposes of the present invention may be made from a wide variety of materials provided that such materials are sufficiently flexible. Preferred materials for this purpose are polyalkylene webs such as polyethylene sheet, polypropylene sheet, and the like. Particularly preferred are webs which are oriented along the narrow dimension of the tabs or webs which have filament reinforcements therein. The elastic anchoring portion of the adhesive tabs suitable for the purposes of the present invention can be made from any suitable elastic material; that is, they may be made from natural or synthetic rubber sheets or webs or the various elastic plastic film materials available.

Pressure-sensitive adhesive layers, such as adhesive coatings, are provided by applying a coating of a pressure-sensitive adhesive composition known in the art to the appropriate surfaces of tab 16, 116, and 216. The applied adhesive should have good tack, good cohesive strength, good resistance to moisture, and good resistance to aging. Illustrative of such adhesive compositions are mixtures of natural and synthetic rubber, zinc oxide and various resins. Also latices of natural or synthetic rubber or water dispersions of acrylic tacky polymers or copolymers may be used. The attachment portion may be an extension of the inelastic anchoring portion with the area of attachment between the two, weakened by scoring or providing a series of perforations in that area. The temporary attachment shall be of sufficient strength to withstand any pulling during machine application to the diaper, but should detach easily in use. Preferably, the temporary attachment should require from about 0.5 to about 4 pounds per inch of width of force to break the temporary attachment. If less than 0.5 pound of force is required to break the temporary attachment, there may be some difficulty in the manufacture of the diaper in that the tape tab structure may not be sufficiently stable to withstand the stresses applied to the tape tab in the high speed manufacturing operation. If more than 4 pounds per inch of width of force is required, then it may be that the mother, when she places the diaper on the wearer in certain instances, may not break the temporary attachment.

Diapers may be made utilizing various types of facing materials, for example, the nonwoven webs made from combinations of short and long fibers as described in U.S. Pat. No. 3,663,348 to Liloia et al, or webs made solely from staple length fibers may be used. The perforated thermoplastic films may also be used as the facing materials for diapers made in accordance with the present invention.

The highly moisture absorbent fibrous pad or batt 22, 122 and 222, which usually is substantially rectangular in shape but smaller than the facing sheet and the backing sheet, can be formed in accordance with the teachings of U.S. Pat. No. 3,612,055 to Mesek et al.

A suitable backing sheet material for the diapers embodying the present invention can be an opaque polyethylene web about 0.001 inch thick. Another suitable material for this purpose is a polyethylene terephthalate web having a thickness of about 0.0005 inch.

In use, a diaper equipped with the adhesive tape tab fasteners of the present invention is applied to the wearer by laying out the diaper on a suitable flat surface and placing the wearer thereon so that the waist underlying end of the diaper is that having the tape tab fastener means. The other end of the diaper then extends downwardly between the infant's legs. The downwardly extending end of the diaper is brought up between the infant's legs to a position contiguous with the front of the waist. The diaper is thereafter secured to the infant by placing the corners of the waist portion about the abdomen and as far around the infant's waist as they will go and by bringing the corners of the underlying end of the diaper into an overlapping relationship with the aforementioned portions so that the diaper snugly encircles the infant's waist. The adhesive fasteners are then prepared for use by pulling the free end of the fastener away from its temporary engagement with release means exposing the adhesive coating which was releasably adhered to release means and separable therefrom. The tabs are then tugged slightly to provide a snug fit breaking the temporary attachment and rendering them elastic in function. The tabs are secured to the diaper in the desired position by simply urging the pressure-sensitive adhesive surface in contact with the adjacent outer surface of the diaper. The applied diaper assumes the configuration illustrated in FIG. 5 and the waist encircling portion of the diaper is elastic providing an improved fit.

The foregoing description and the drawings are illustrative but are not to be taken as limiting, still other variations and modifications are possible without departing from the spirit and scope of the present invention.

I claim:

1. A disposable diaper having a facing sheet defining a diaper inside surface for direction toward the wearer, a moisture-impervious backing sheet substantially co-extensive with said facing sheet and defining a diaper outside surface, an absorbent panel positioned between said facing sheet and said backing sheet, and adhesive tape tab fastening means which comprises:
   (a) a first anchoring portion secured to the diaper outside surface at a marginal portion thereof;
   (b) a second anchoring portion secured to the diaper inside surface at a marginal portion thereof, said second anchoring portion being made from elastic web material;
   (c) an attachment portion temporarily attached to the first anchoring portion and adhesively secured to said second anchoring portion, said temporary attachment being such that it is broken before the attachment portion can be detached from said second anchoring portion; and
   (d) said attachment portion having a free working end provided with a layer of pressure-sensitive adhesive on one face thereof.

2. A disposable diaper according to claim 1 wherein the attachment portion attached to the first anchoring portion is susceptible of being broken by a force of from between about 0.5 pound per inch of width and about 4 pounds per inch of width.

3. A disposable diaper having a facing sheet defining a diaper inside surface for direction toward the wearer, a moisture-impervious backing sheet substantially co-extensive with said facing sheet and defining a diaper outside surface, an absorbent panel positioned between said facing sheet and said backing sheet, and an adhesive tape tab fastening means which comprises:
   (a) a first anchoring portion secured to the diaper outside surface at a marginal portion thereof;
   (b) a second anchoring portion secured to the diaper inside surface at a marginal portion thereof, said second anchoring portion being made from elastic web material;
   (c) an attachment portion temporarily attached to the first anchoring portion and adhesively secured to said second anchoring portion, said temporary attachment being such that it is broken before the attachment portion can be detached from said second anchoring portion;
   (d) said attachment portion having a free working end provided with a layer of pressure-sensitive adhesive on one facing thereof;
   (e) release means on the outside surface of the second anchoring portion; and (f) said free end being adhered to said release means whereby said free end is available for use in securing the diaper about a wearer.

4. A disposable diaper according to claim 3 wherein the attachment portion temporarily attached to the first anchoring portion has its temporary attachment capable of being broken by a force of about 0.5 pound per inch of width to 4 pounds per inch of width.

5. A disposable diaper according to claim 3 or 4 wherein the second anchoring portion is substantially shorter than the first anchoring portion.

6. A disposable diaper according to claim 3 or 4 wherein the first anchoring portion is secured to the outside surface and to the second anchoring portion.

* * * * *